(12) United States Patent
Hunter

(10) Patent No.: US 11,963,890 B2
(45) Date of Patent: Apr. 23, 2024

(54) PROSTHETIC HAND

(71) Applicant: EPIC INVENTING, INC., Los Angeles, CA (US)

(72) Inventor: Mark Hunter, Los Angeles, CA (US)

(73) Assignee: EPIC INVENTING, INC., Los Angeles, CA (US)

( * ) Notice: Subject to any disclaimer, the term of this patent is extended or adjusted under 35 U.S.C. 154(b) by 377 days.

(21) Appl. No.: 16/973,180

(22) PCT Filed: Jun. 7, 2019

(86) PCT No.: PCT/IB2019/054776
§ 371 (c)(1),
(2) Date: Dec. 8, 2020

(87) PCT Pub. No.: WO2019/234707
PCT Pub. Date: Dec. 12, 2019

(65) Prior Publication Data
US 2021/0251779 A1     Aug. 19, 2021

(30) Foreign Application Priority Data
Jun. 8, 2018   (GB) ...................... 1809492

(51) Int. Cl.
*A61F 2/70*  (2006.01)
*A61F 2/54*  (2006.01)
(Continued)

(52) U.S. Cl.
CPC ................ *A61F 2/586* (2013.01); *A61F 2/70* (2013.01); *B25J 15/0009* (2013.01);
(Continued)

(58) Field of Classification Search
CPC .... A61F 2/586; A61F 2002/587; B25J 15/024
See application file for complete search history.

(56) References Cited

U.S. PATENT DOCUMENTS 2,629,107 A   2/1953 Becker
3,631,542 A   1/1972 Potter
(Continued)

FOREIGN PATENT DOCUMENTS

CN        108272537        7/2018
DE   10 2012 003 360 A1 *  8/2013   .............. B25J 15/12
(Continued)

OTHER PUBLICATIONS

DE 10 2012 003 360 A1 (Aug. 22, 2013)—machine translation obtained from espacenet.*

(Continued)

*Primary Examiner* — David H Willse
(74) *Attorney, Agent, or Firm* — Meunier Carlin & Curfman LLC

(57) ABSTRACT

The present invention provides a prosthetic device (10) having an anchor portion (30) in combination with a base portion (12) which is connected to the anchor portion (30). An elongate digit (14) is coupled to a first portion of a pivot connection (16a) mounted on the base portion (12), whilst a second portion of a pivot connection (16b) is mounted on the proximal end (14a) of the digit (14) and is connected to the first portion (16a) of the pivot connection (16). A linear actuator (40) within the elongate digit (14) has a first portion (40a) secured to the elongate digit (14) for movement therewith and a second portion (40b) remote therefrom and axially movable relative thereto and is operable with said pivot connection (16) to cause pivotal movement of the digit (14) around the pivot connection (16a, 16b) upon axial movement of the second portion (40b) of the linear actuator (40).

15 Claims, 8 Drawing Sheets

(51) Int. Cl.
    *A61F 2/58*     (2006.01)
    *B25J 15/00*     (2006.01)
    *B25J 15/02*     (2006.01)
    *A61F 2/50*     (2006.01)
    *A61F 2/68*     (2006.01)
    *A61F 2/76*     (2006.01)
    *B25J 15/10*     (2006.01)

(52) U.S. Cl.
    CPC ..... *B25J 15/024* (2013.01); *A61F 2002/5018* (2013.01); *A61F 2002/5038* (2013.01); *A61F 2002/5043* (2013.01); *A61F 2002/5072* (2013.01); *A61F 2002/587* (2013.01); *A61F 2002/6827* (2013.01); *A61F 2002/701* (2013.01); *A61F 2002/704* (2013.01); *A61F 2002/7635* (2013.01)

(56) References Cited

U.S. PATENT DOCUMENTS

| | | |
|---|---|---|
| 2013/0175816 A1 | 7/2013 | Kawasaki et al. |
| 2013/0253705 A1 | 9/2013 | Dalley et al. |
| 2016/0089251 A1 | 3/2016 | Mandl et al. |
| 2016/0235555 A1 | 8/2016 | Hunter |
| 2018/0064563 A1 | 3/2018 | Gill |
| 2018/0256367 A1 | 9/2018 | Bai |
| 2018/0296368 A1 | 10/2018 | Gill |

FOREIGN PATENT DOCUMENTS

| | | | |
|---|---|---|---|
| GB | 2488365 A | * 8/2012 | ............. A61F 2/586 |
| SU | 810234 | 3/1981 | |
| WO | 2015/128604 | 9/2015 | |
| WO | 2015/138968 | 9/2015 | |
| WO | 2017/084638 | 5/2017 | |
| WO | 2018/042215 | 3/2018 | |

OTHER PUBLICATIONS

International Search Report and Written Opinion dated Feb. 28, 2020, from International Application No. PCT/IB2019/054776, 21 pages.
Combined Search and Examination Report under Section 17 and 18(3) dated Jun. 8, 2020, from related GB application No. 1809492.0, 12 pages.
Examination Report issued for Application No. GB1809492.0, dated Feb. 15, 2021.
Search Report issued for Application No. GB1809492.0, dated Feb. 15, 2021.
Examination Report issued for Application No. GB1809492.0, dated Jan. 12, 2022.

* cited by examiner

PROSTHETIC HAND

The present invention relates to a prosthetic hand having one or more digits and relates particularly but not exclusively to an arrangement having compound movement of one or more or more of the digits such as may be made for and used by human amputees and more particularly to those amputees that have lost one or more digits on a hand.

Prosthetic hands having a plurality of movable digits are well known and one such device is described in WO2015138968A1 to the same inventor as the present invention. Such devices generally comprise one or more digits which are each engineered so as to replicate, as far as possible, the natural movement of a real digit. For example, a prosthetic finger will be provided with three portions each linked to the other by means of an articulated joint and being shaped and sized such as to replicate as near as possible a natural finger. A prosthetic thumb may be provided with just two portions which are linked to each other by a similar articulated joint and similarly shaped and sized to replicate, as near as possible, a natural finger. Each of the prosthetic fingers and/or the prosthetic thumb is joined to the main body of the prosthetic hand by means of a further linkage so as to allow the respective finger or thumb to pivot relative to the main body of the prosthetic hand. To date the joints have tended to be hinged arrangements which provide sufficient movement to allow the hand to perform all the essential functions but prevent the prosthetic hand from functioning in the manner of a natural hand and prevents the prosthetic hand replicating the more natural and less restricted movement of a natural hand. In addition, the actuators for such hands tend to be employed for each portion of each digit and, hence, the actuation system can be more bulky and heavy than might be desired. This problem would be compounded if further actuators were to be provided in order facilitate any additional movement.

It is an object of the present invention to provide a prosthetic hand having one or more digits in which one or more of the one or more digits is able to move in a controlled manner by rotation or lateral movement in addition to the already established single plane motion of existing prosthetics. It is a further object of the present invention to provide an actuator for such prosthetic digits which is able to provide a driving motion in more than one plane and/or about one or more axis.

Accordingly, the present invention provides a prosthetic device comprising an anchor portion that may comprise a bearing part and a housing part. A base portion may have a proximal side and a distal side connected to said anchor portion through a bearing part. An elongate digit may have a proximal end and a distal end and extend along or substantially along a longitudinal axis X. A first portion of a pivot connection may be mounted on the base portion. A second portion of a pivot connection may be mounted on the proximal end of the digit and may be connected to the first portion of the pivot connection. An actuator may be included to cause pivotal movement of said digit around said pivot connection. Said base portion may include a second longitudinal axis X2 extending between said proximal side and said distal side and a bearing between the base portion and said anchor portion. Said base portion may be mounted to said anchor portion via said bearing and may be rotatable about said second longitudinal axis X2.

In an alternative embodiment, the prosthetic device may include a rotation actuator for causing rotational movement of the digit within said bearing about said second longitudinal axis X2.

In a further alternative embodiment, said rotational actuator of the prosthetic device may comprise a motor mounted within the digit. The prosthetic device may further include a torque tube connected at a first end to the rotational actuator and at a second end to the anchor.

In a further alternative embodiment of the prosthetic device said digit may comprise a thumb.

In a further alternative embodiment, the prosthetic device may have a palm portion and wherein said anchor portion may be mounted on said palm portion.

In a further alternative embodiment, the prosthetic device may include a plurality of prosthetic digits, such as described herein.

In a further alternative embodiment, the prosthetic device may include a controller for controlling the operation of one or more of said digits.

In a further alternative embodiment the prosthetic device may comprise a prosthetic thumb and a plurality of prosthetic fingers. Said controller may operate to cause rotation of the prosthetic thumb in combination with pivotal movement of said thumb as said thumb moves towards said prosthetic fingers.

In a further alternative embodiment of the prosthetic device said bearing may comprise a hollow bearing having an internal aperture for receiving power or actuation connections.

According to a second aspect of the present invention there is also provided a prosthetic device comprising an anchor portion; a base portion having a proximal side and a distal side and being connected to said anchor portion. An elongate digit may have a proximal end and a distal end extending along a longitudinal axis X. A first portion of a pivot connection may be mounted on the base portion. A second portion of a pivot connection may be mounted on the proximal end of the digit and may be connected to the first portion of the pivot connection. A linear actuator within the elongate digit may have a first portion secured to the elongate digit for movement therewith and a second portion remote therefrom and axially movable relative thereto and being operable with said pivot connection, thereby to cause pivotal movement of said digit around said pivot connection upon axial movement of said second portion of said linear actuator.

In an alternative embodiment of the prosthetic device said second portion of said linear actuator may include one or more transfer pivot pins extending outward therefrom. Said base portion may include one or more apertures for receiving said one or more transfer pivot pins. Wherein said apertures may be radially displaced relative to the pivot connection such as to allow for pivotal movement of said digit about said pivot connection upon axial translation of said second portion of the linear actuator.

In an alternative embodiment of the prosthetic device said first side and second side of said digit may be contained between said first and second sides of said base portion. Wherein each of said first and second sides may include a slot or means defining a slot, each of said slots extending along said longitudinal axis X of said digit and may receive respective second transfer pins therethrough. In a further alternative embodiment of the prosthetic device said base portion may include a second longitudinal axis X2 extending between said proximal side and said distal side and may further include a bearing between the base portion and said anchor portion. Said base portion may be mounted to said anchor portion via said bearing and may be rotatable about said second longitudinal axis X2.

In a further alternative embodiment, the prosthetic device may include a rotation actuator for causing rotational movement of the digit within said bearing about said second longitudinal axis X2.

In an alternative embodiment of the prosthetic device said rotational actuator includes a torque tube connected at a first end to the rotational actuator and at a second end to the anchor at point.

In an alternative embodiment of the prosthetic device the torque tube may extend through said bearing.

In an alternative embodiment of the prosthetic device said digit may comprise a thumb.

In an alternative embodiment the prosthetic device may have a palm portion, wherein said anchor portion may be mounted on said palm portion.

In an alternative embodiment of the prosthetic device may include a plurality of prosthetic digits.

In an alternative embodiment the prosthetic device may include a controller for controlling the operation of one or more of said digits.

In an alternative embodiment the prosthetic device may include a first load sensor for sensing external resistance to pivotal movement of said one or more digits.

In an alternative embodiment the prosthetic device may include a second load sensor for sensing external resistance to rotational movement of said one or more digits.

In a further alternative embodiment, the prosthetic device may comprise a prosthetic thumb and a plurality of prosthetic fingers. Said controller may operate to cause rotation of the prosthetic thumb in combination with pivotal movement of said thumb as said thumb moves towards said prosthetic fingers.

In a further alternative embodiment of the prosthetic device said bearing may comprise a hollow bearing having an internal aperture for receiving power or actuation connections.

The above-mentioned arrangements allow the digit to be mounted onto an anchor portion which can then be mounted on, for example, a palm portion and a plurality of such digits and base portions may be mounted onto a common anchor portion such as, for example, a palm portion of a prosthetic hand. The arrangement also allows for the positioning of the actuation motor within the digit itself which allows for the creation of a slimmer and more aesthetically pleasing finished product that more easily replicates the natural shape and dimensions of a human hand. In particular, the arrangement lends itself to use in the production of smaller hands such as may be required for children or adults with naturally smaller hands. The base portion also allows for a further degree of freedom of movement described later herein.

The present invention will now be more particularly described with reference to the accompanying drawings, in which.

Figure 1:
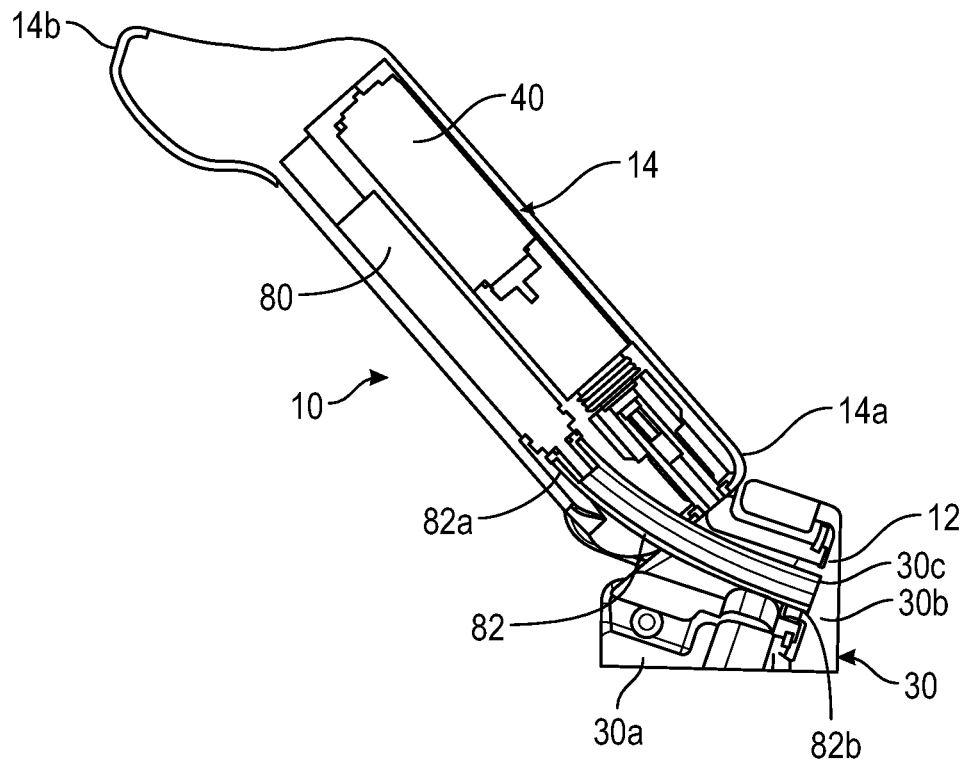
FIG. 1 is a first cross-sectional view of a digit according to aspects of the present invention in a first, raised, position.

Referring now to the drawings in general but with particular reference to FIGS. 1 to 5, a prosthetic device 10 may include one or more thumbs and/or fingers referred to herein generally as digits 14, each of which is mounted on a base portion 12 which, in turn, is mounted onto an anchor 30. The anchor 30 may comprise the main body or palm of a prosthetic hand or may comprise a sleeve or cover to be placed over a portion of the user's natural hand if portions thereof are present. Such may be the case where the patient has lost one or more digits but not an entire hand. The one or more digits 14 are each provided with an actuation mechanism or motor 40, 80 for creating one or other or both of pivotal and/or rotational movement of the digit in question 12. These mechanisms 40, 80 may be provided as separate units, as shown herein, or may be combined as one unit if so desired and each are described in more detail later herein. The digits 14 are each provided with a proximal end 14a closest to the anchor 30 and a distal end 14b remote therefrom. The proximal end 14a is pivotally connected to the base portion 12 by means of a pivot shown generally at 16 and also described in more detail later herein. One or more of the one or more digits may have a base portion 12 which is connected to the anchor 30 by means of a rotational mount in the form of, for example, a bearing shown generally at 60 which facilitates the base portion 12 and the digit 14 rotating about a second axis X2. Again, this feature is described in more detail later herein. It will be appreciated that the arrangement of mounting the digit 14 to a base portion 12 which is, in turn, connected to an anchor 30 which forms part of the main body of a prosthetic hand may be used with or without the further feature of the base portion (and hence the digit) being rotatable about the second longitudinal axis X2. It will also be appreciated that the rotational aspect of the present invention may be incorporated into prosthetic digits without the specific actuator arrangement as shown in this particular document but that a significant advantage may be gained by incorporating the two in one product.

Figure 2:
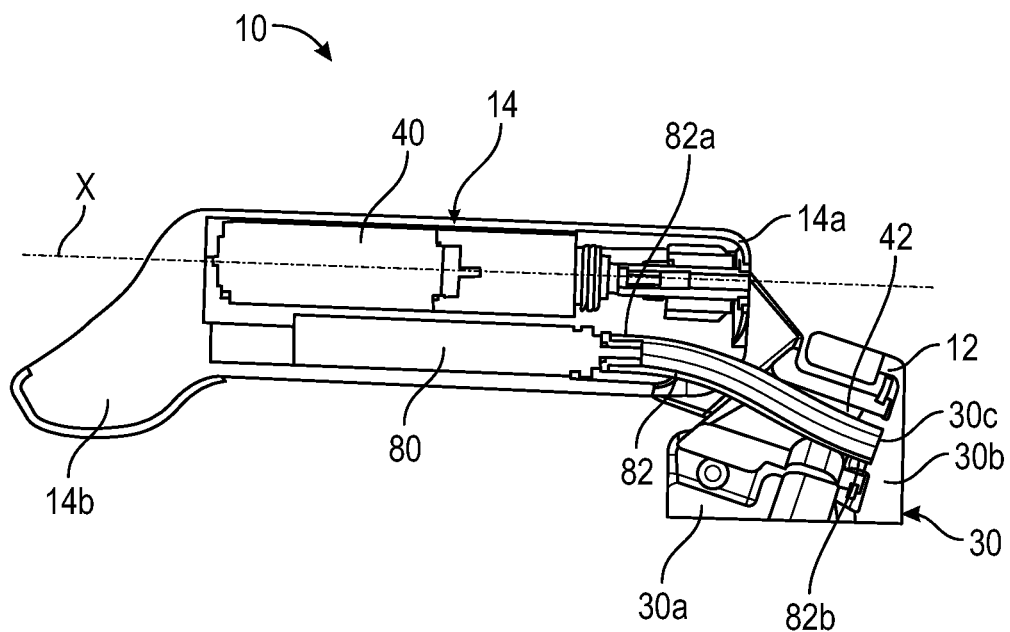
FIG. 2 is a cross-sectional view of the digit of FIG. 1 but in a second, lowered, position.
Figure 3:
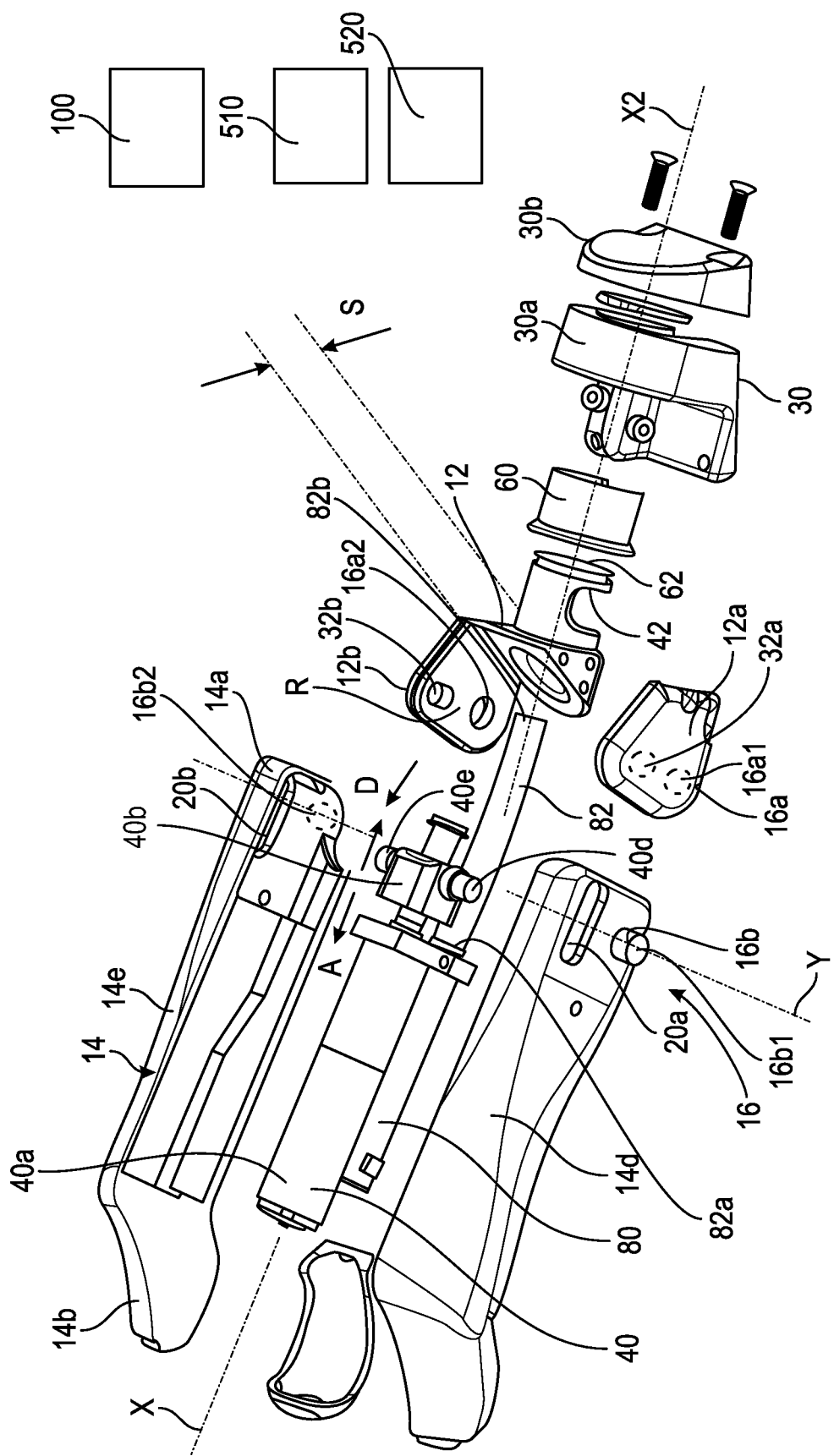
FIG. 3 is an exploded view of the digit shown in FIGS. 1 and 2.
Figure 4:
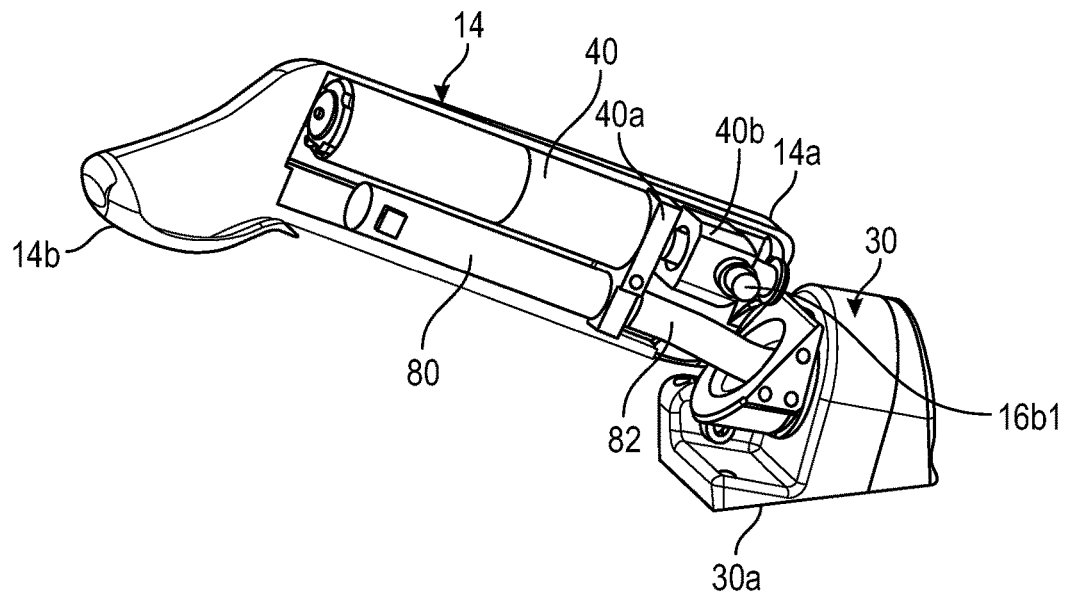
FIG. 4 is an isometric view of the digit of the above-mentioned figures.
Figure 5:
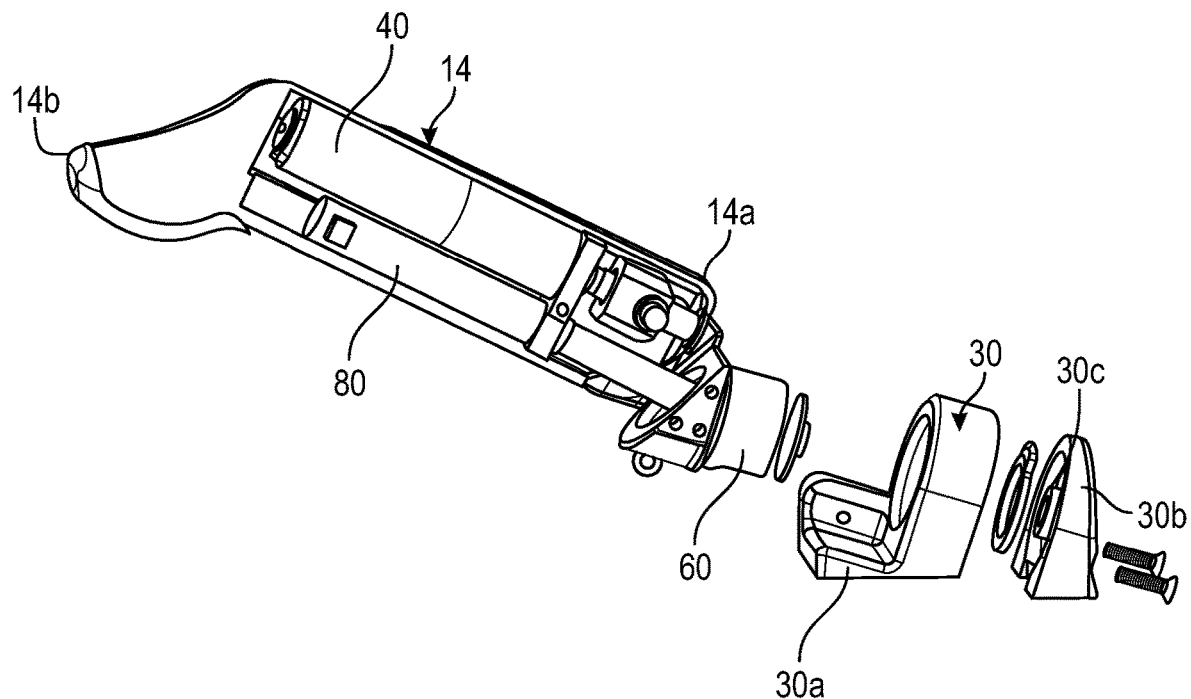
FIG. 5 is a partially disassembled arrangement of the above-referenced digit.

Referring now more particularly to FIG. 3 which is an exploded view of the digit 14 of FIGS. 1 and 2, it will be seen that the digit has a longitudinal axis X and is mounted at a proximal end 14a to the base 12 by means of a pivot 16 operational around a third axis Y which is generally perpendicular to axis X and which may comprise a first portion 16a forming, for example, an aperture on the base 12 and a second portion 16b on the proximal end 14a of the digit 14 itself. in the particular arrangement of the drawings, said base portion 12 includes first and second sides 12a, 12b projecting therefrom in a common direction D and being spaced apart from each other by an amount S and wherein each side 12a, 12b includes a first portion of the pivot connection 16a and wherein said digit 14 includes a first side 14d and a second side 14e and wherein said first side 14d includes a first portion 16b1 of the pivot connection 16b and said second side 14b of the digit 14 includes a second portion 16b2 of the pivot connection 16b and wherein each of said second portions 16b1, 16b2 of the pivot connection 16b extend into respective first portions 16a of the pivot connection 16 when assembled. The digit 14 further includes a linear actuator 40 contained therein and having a first portion 40a secured to the elongate digit 14 for movement therewith and a second portion 40b remote therefrom and axially movable relative thereto, as shown by arrow A in FIG. 3.

The second portion 40b of said linear actuator 40 may include one or more transfer pivot pins 40d, 40e extending outward therefrom whilst said base portion 12 may include one or more apertures 32a, 32b for receiving said one or more transfer pivot pins 40d, 40e. The apertures 32a, 32b are radially displaced by an amount R relative to the pivot connection 16 such as to allow for pivotal movement of said digit 14 about said pivot connection 16 upon axial translation of said second portion 40b of the linear actuator 40. In essence, the second end of the actuator 40a, pushes against apertures 32a, 32b and as the other end of the linear actuator 40 is connected to the digit 14 this will cause the digit 14 to pivot about the pivot connection 16 and axis X. This movement will cause the digit 14 to replicate the opening and closing of the digit and control of the linear actuator may be initiated in accordance with a desired control sequence or instruction as and when desired from a controller shown schematically at 100.

As can be seen more clearly in some of the later drawings, the proximal end 14a of the digit(s) 14 are located such that the first side and second sides 14d, 14e of said digit are contained between said first and second sides 12a, 12b of said base portion 12.

As mentioned above, each of said first and second sides 12a, 12b include respective apertures 32a, 32b for receiving respective second portions 40d, 40b of the pivot 16. The first and second portions 14d, 14e of the digit 14 are each provided with a respective slot 20a, 20b at their respective proximal ends 14a extending along said longitudinal axis X of said digit 14 and these slots 20a, 20b receive respective transfer pivot pins 40d, 40e of actuator 40 therethrough such as to allow the linear actuator 40 to be connected to the anchor 30. The slots 20a, 20b extend for a sufficient length as to allow for the full and free movement of the linear actuator as and when desired. Movement of transfer pivot pins 40d, 40e will cause the digit 14 to pivot about pivot connection 16 as will be described in more detail later herein.

The base portion 12 may, in one embodiment of the invention, also include a second longitudinal axis X2 extending between said proximal side 12a and said distal side 12b and a bearing 60 may be provided between the base portion 12 and said anchor portion 30 such that said base portion 12 is mounted to said anchor portion 30 via said bearing 40 and rotatable about said second longitudinal axis X2 as and when required. The bearing 60 may comprise a hollow bearing include an internal aperture 62 for allowing the passage of portions of a rotational actuator or electrical or operational supply cabling to be provided therethrough.

This capability is new to prosthetic digits and may be used to provide the user with a higher degree of motion and possibly a greater degree of feedback than has been previously known in the field of prosthetic digits. The device 10 may also include a rotation actuator 80 for causing rotational movement of the digit 14 within said bearing 60 about said second longitudinal axis X2. Such a rotational actuator 80 may be housed within the digit itself 14 or may be mounted remotely therefrom, although advantages of compactness and controllability will be present if the rotational actuator is mounted within the digit itself 14. Whilst there are a number of rotational actuator arrangements that could be used, it has been found that an arrangement in which the rotational actuator 80 is housed within the digit and anchored relative thereto will allow for the use of a torque tube 82 extending therefrom which can be connected at a first end 82a to the rotational actuator 80 and at a second end to the anchor 30. The anchor 30 is comprised of two parts, a rotation housing 30a wherein the base portion 12 pivots around axis X2, and a housing 30b wherein the torque tube proximal end 82b is connected. The torque tube 82 is connected at its first end 82a to the rotation actuator 80, and at its second end 82b to the housing 30b at point 30c. Housing 30b and the rotation housing 30a are both connected to the palm of the hand 200. The torque tube 82 may extend through bearing 60 or may pass around it if space permits. The torque tube may also be hollow and include a first opening 82a thereinto for receiving any electrical wiring or connections thereinto and a second opening 82b for allowing any such electrical wiring or connections to be routed out of the torque tube 82. The first and second openings 82a, 82b may be on the first and second ends 82a. Preferably, the torque tube is sufficiently flexible so as to allow for the desired degree of movement of the digit 14 but is sufficiently resistant to rotation as to ensure the desired rotational movement is transmitted. Such an arrangement would allow for the transmission of rotational torque from the rotational actuator 80 through the torque tube 82 to the anchor 30 at which point it is reacted and this will cause the base portion 20 and digit 14 to rotate about axis X2. Again, the rotational actuator 80 may be operably connected to a controller shown schematically at 100 and may be operated by said controller as and when desired.

The above design provides a prosthetic device 10 with one or more digits 14 which can, if desired, have compound movement in the sense that they can each move about two axes, one of which replicates the normal bending of a human digit and one of which replicates the rotational movement which is normally associated with a thumb but which could be used on the fingers of a prosthetic device. It also provides a prosthetic device which is able to be relatively compact and may allow for the production of smaller prosthetic devices than has been known until now.

The above arrangement may be added to in a number of ways. For example, the digit 14 may be provided with a first load sensor 510 (which may be a microprocessor) for sensing external resistance to pivotal movement of said one or more digits 14. Such a sensor may be used to provide feedback on the strength of grip being applied to an object. The arrangement may also include a second load sensor (520) for sensing external resistance to rotational movement of said one or more digits (14). Again, this may be used to provide feedback on the strength of any grip being asserted by the digit. Still further, the digit may be provided with an overload mechanism in the form of spring-loading of the mechanisms arranged such as to provide a degree of resilient resistance to motion which would accommodate any overload through resilient motion. In the example of the rotational arrangement using a torque tube 82, the resilience to rotational motion could be incorporated by way of the torque tube itself being a spring or having resilient properties. In the example of the linear actuator 40, the resilience may be built into the mechanism by which the movable second portion 40b is connected to the static first portion 40a which, again, may include resilient members or spring arrangements.

In a preferred embodiment the torque tube 82 allows the electrical cables from actuators 40 and 80 to pass through it, thus allowing a smooth and minimally moving path.

Thus far we have described a single digit arrangement 14 forming one or other of a thumb or finger of a prosthetic device. It will, however, be appreciated that a partial or compete prosthetic hand may be assembled from or including the above-described components. A partial hand may comprise one or more digits whilst an entire hand would comprise all the digits in the form of both fingers and thumbs. It will be appreciated that aspects of the present invention may be provided on the thumb and/or the fingers of a prosthetic device and that further actuation mechanisms may be provided in addition to those described herein.

Figure 6:
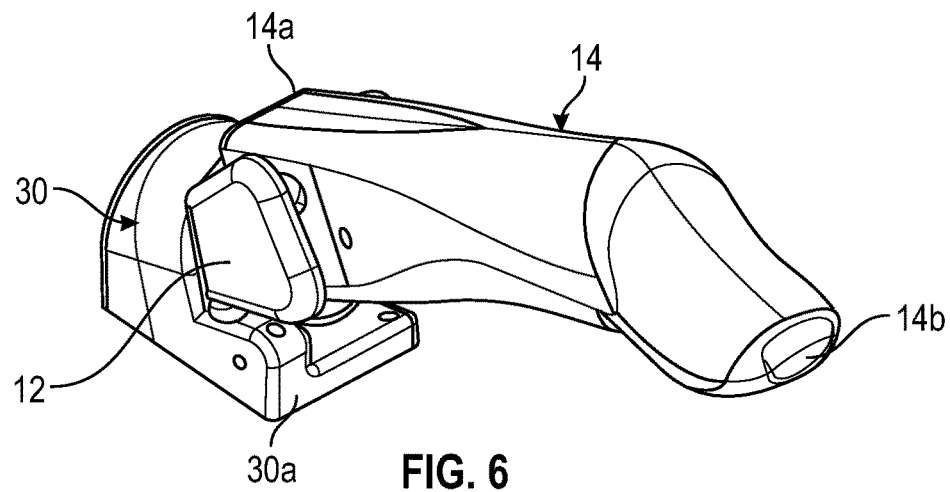
FIGS. 6 to 8 are front isometric views of the digit referred to above showing various rotational positions thereof.
Figure 7:
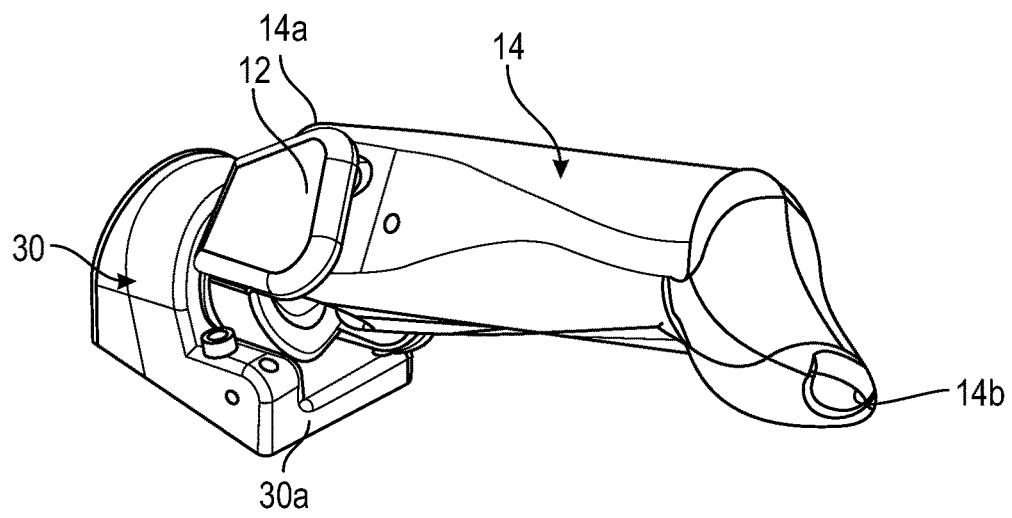
Figure 8:
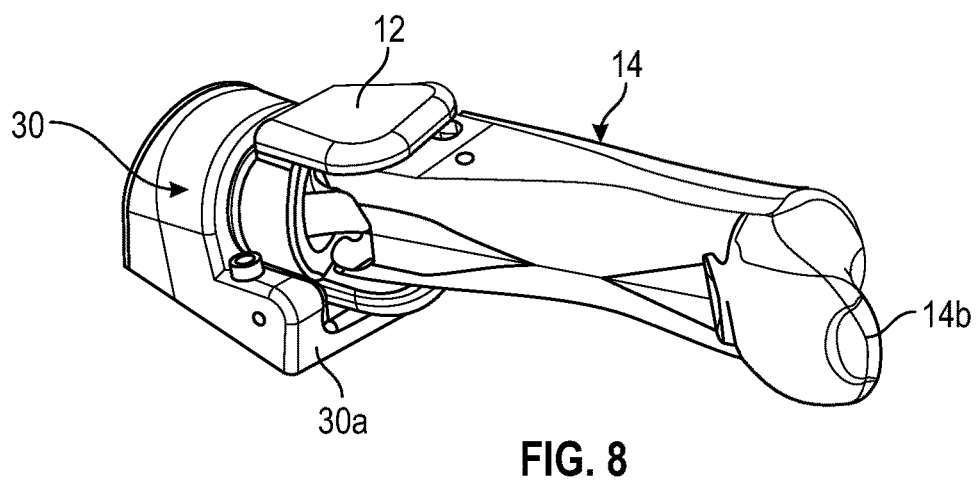
Figure 9:
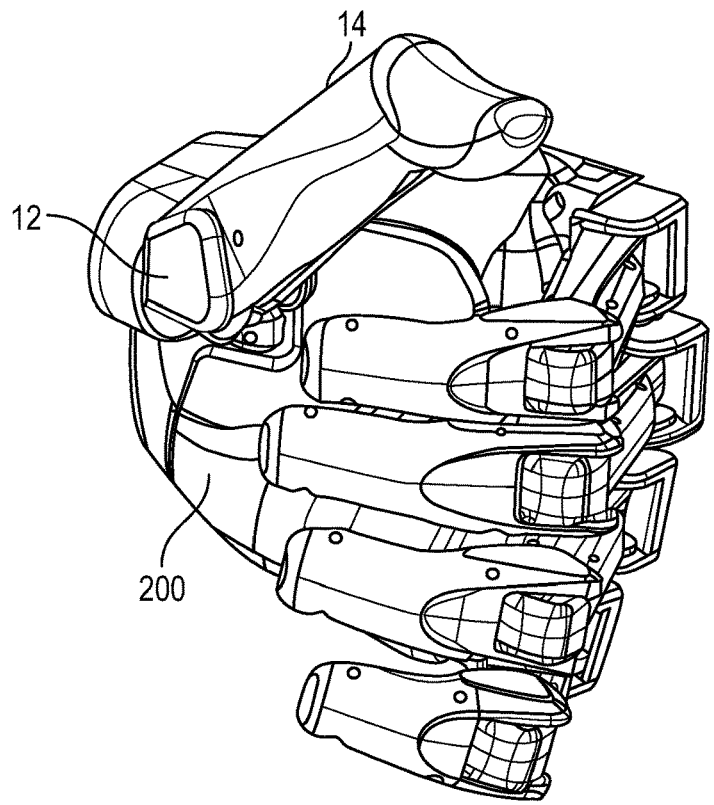
FIGS. 9 to 16 illustrate a full prosthetic hand incorporating elements of the present invention and showing a plurality of different positions of the one or more digits provided thereon.
Figure 10:
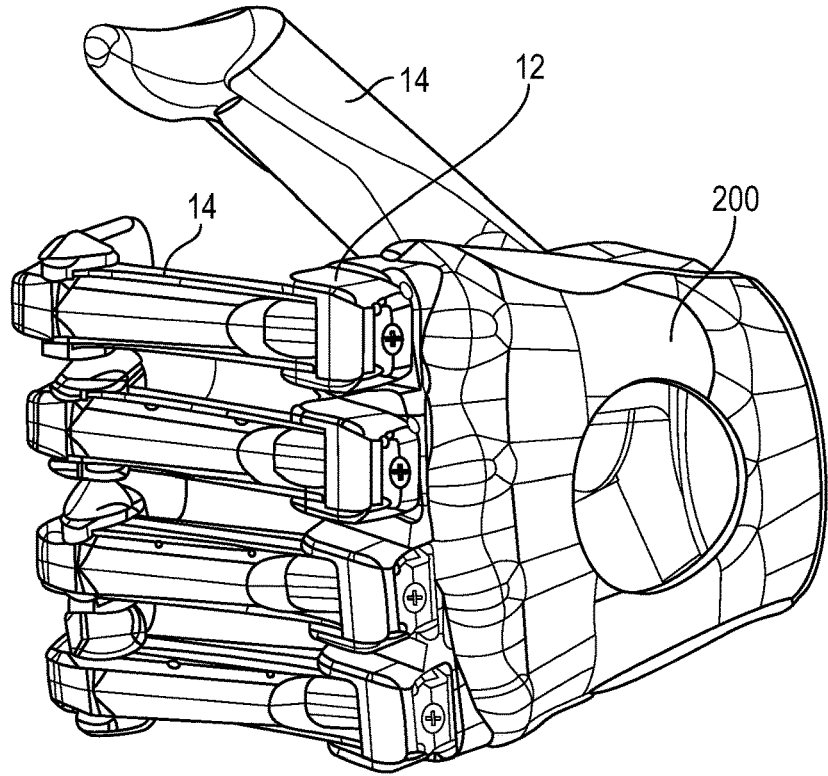
Figure 11:
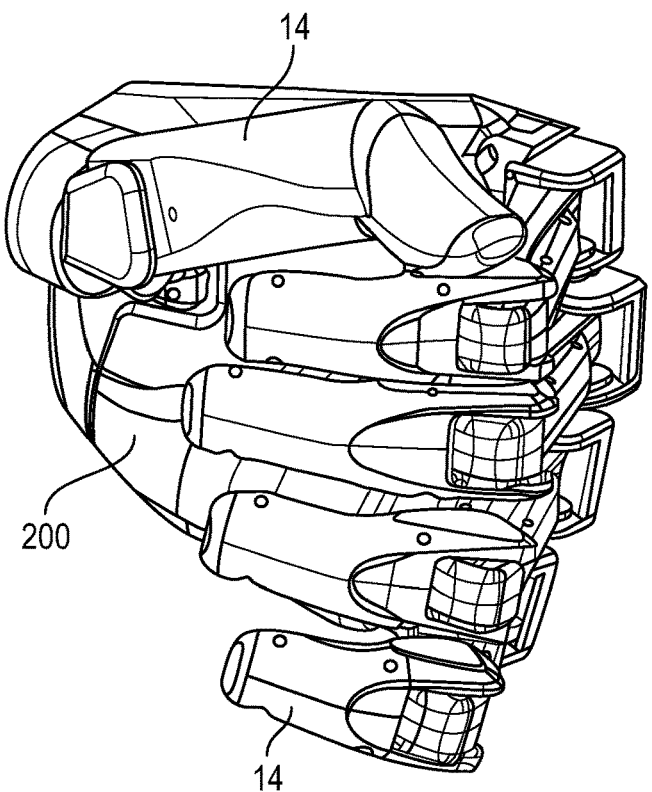
Figure 12:
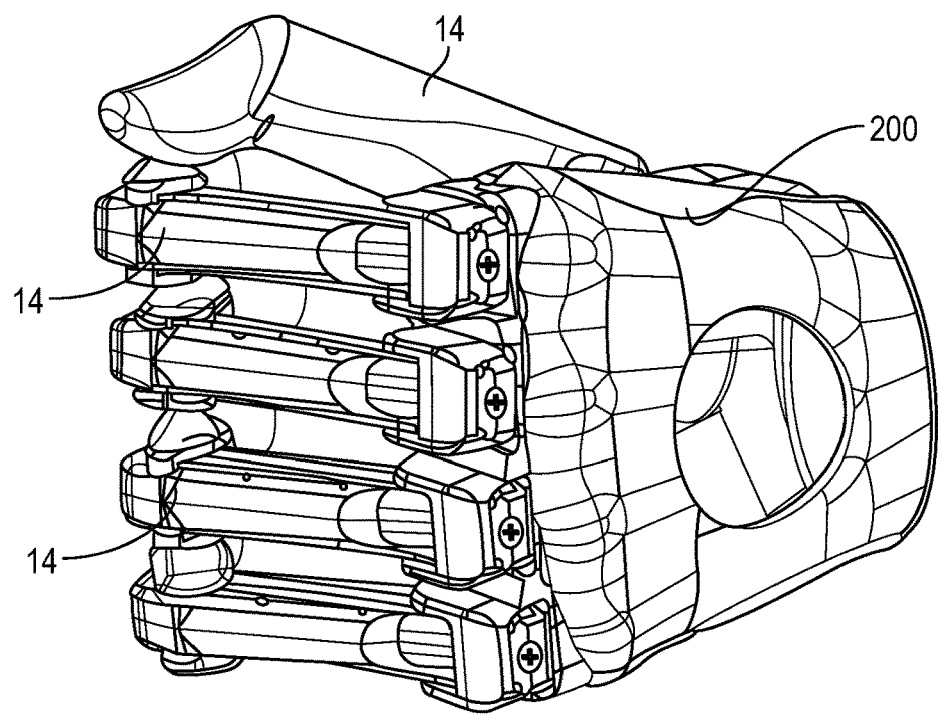
Figure 13:
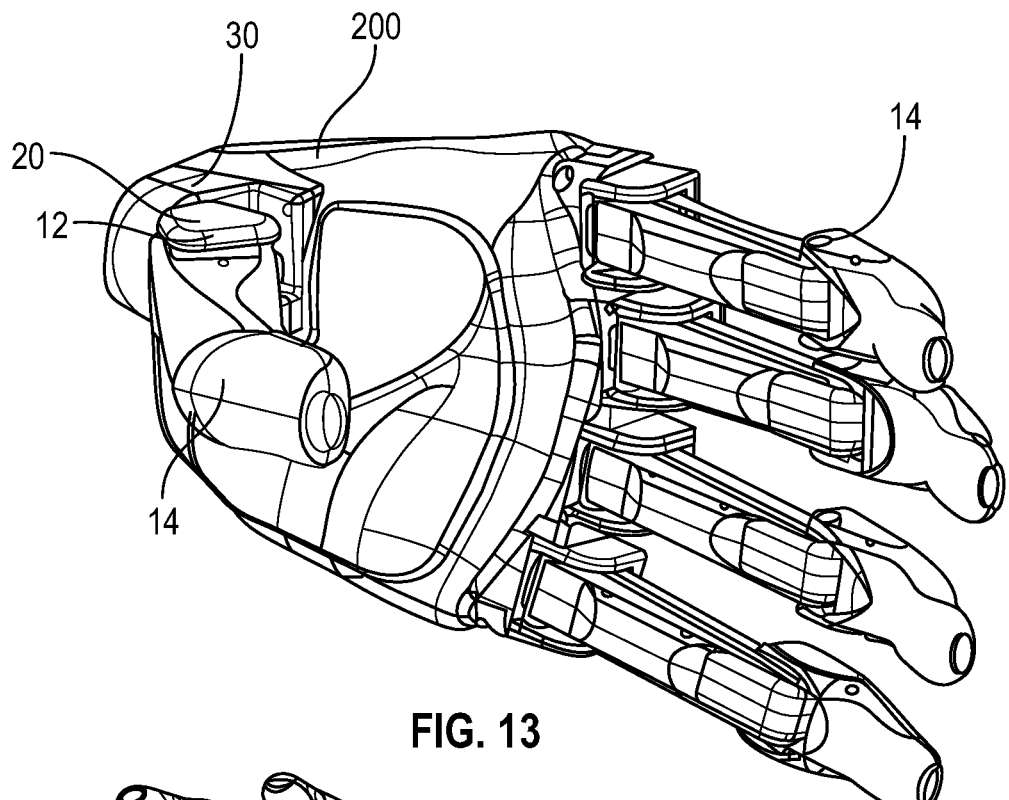
Figure 14:
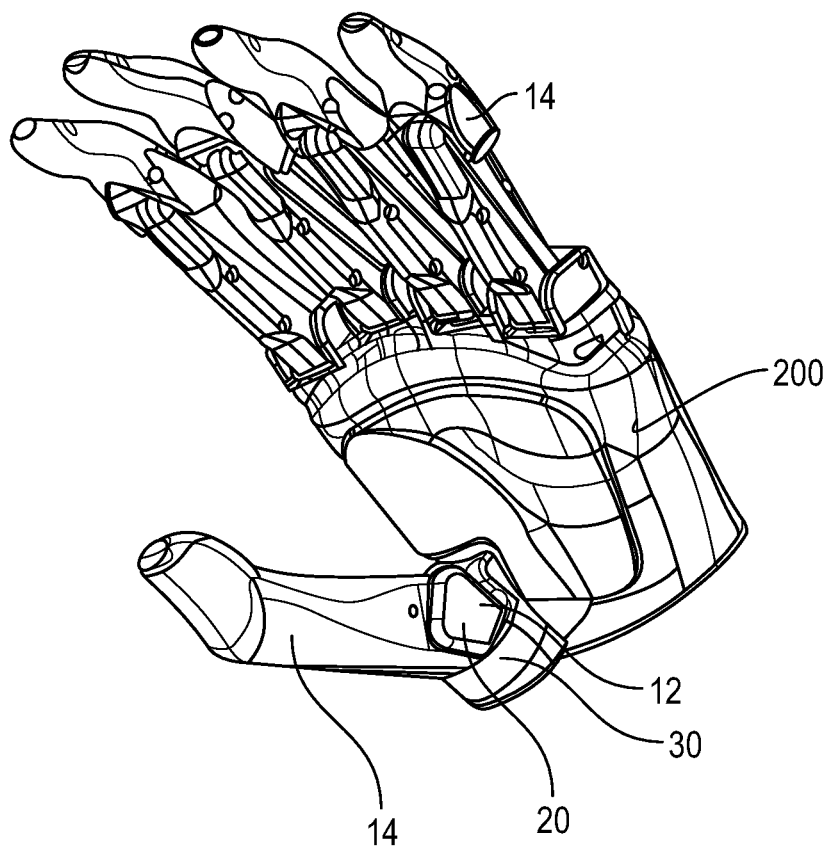
Figure 15:
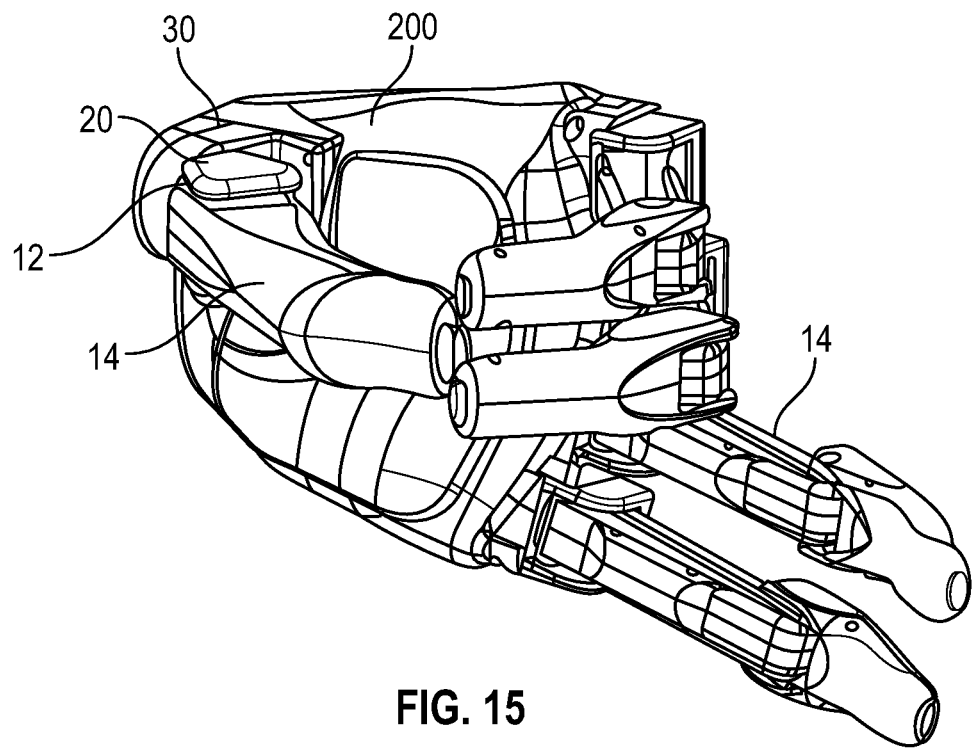
Figure 16:
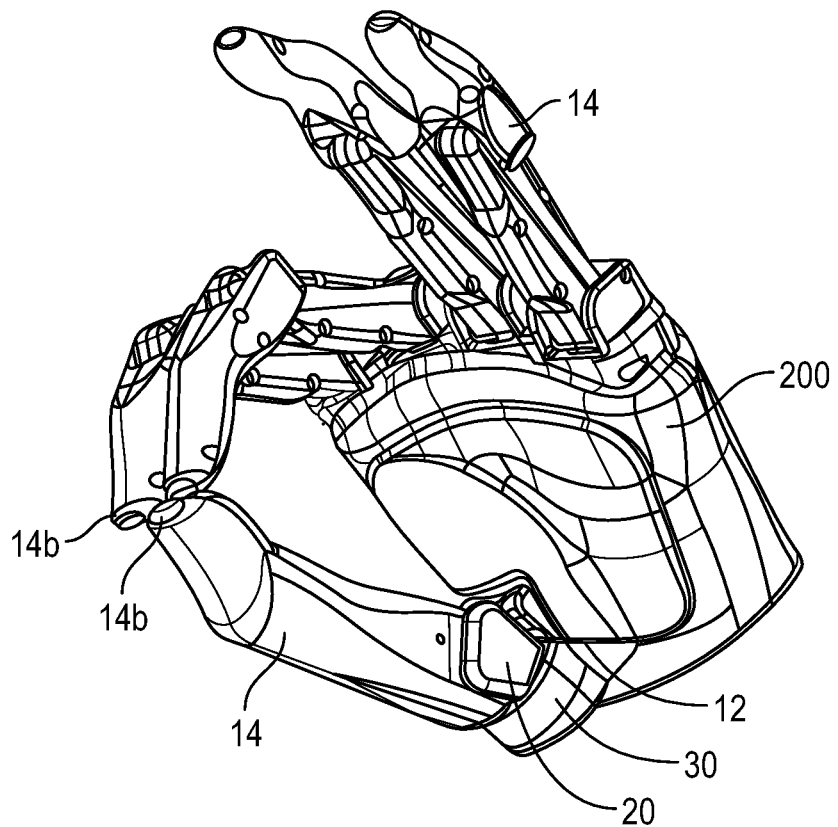

Rotational movement of the digit 14 is shown in FIGS. 6 to 8 whilst the opening and closing of a full prosthetic hand is shown in FIGS. 9 to 16. From these figures it will be appreciated that a full or partial prosthetic hand may be provided simply by attaching one or more of the above-mentioned digits 14 onto a socket portion or glove portion for fitting over the hand of a patient requiring less than a full prosthetic replacement of digits or a palm portion of a prosthetic device where a full set of digits is required. For convenience each of the glove portion and palm portion will be referred to hereafter as a palm portion and provided with a single reference number 200. Those skilled in the art will, however, appreciate that the digit and the following may be applied to either the glove or full palm arrangement. In each of the arrangements of FIGS. 9 to 16 the base portion 12 of each of the one or more digits 14 is connected to the anchor 30 as described above but now each anchor 30 is, itself, mounted onto the glove/palm 200 in a pattern designed to replicate a full hand or replace missing digits if a partial replacement is desired. Each digit is as described above but it will be appreciated that one may dispense with the rotational element of the digit 14 when the invention is applied to the fingers as fingers may not need to have rotational movement capability. The thumb may also be provided without rotational capability, but this is not a preferred arrangement of the present invention.

The controller 100 is connected to each of the linear and/or rotational actuators 40, 80 in each digit 14 to cause the supply of current thereto in the manner required to control the digit. Such control is already well known in relation to simple opening and closing of the digit but is not known for rotational control. Control of the digits 14 may be undertaken in any one of a number of ways but generally requires the input of control signals to open and close the digits 14 in accordance with a pre-determined movement profile or in response to an individual tailored request for movement when, for example, the hand is required to provide a certain grip profile. FIGS. 9 to 16 illustrate that the present invention is able to replicate the full degree of movement of the human hand including the ability to have the thumb rotate as it moves towards the fingers of the hand on the other side of the palm. Such compound movement of the thumb and possibly also one or more of the fingers will mean that the present prosthetic hand is able to provide grip patterns that have not been previously available to a patient.

The invention claimed is:

1. A prosthetic device including an elongate digit comprising:
   a) an anchor portion having a bearing part and a housing part;
   b) a base portion operable to rotate the elongate digit having a proximal side and a distal side and being connected to said anchor portion through the bearing part;
   c) the elongate digit having a proximal end and a distal end and extending along a longitudinal axis X;
   d) a first portion of a pivot connection mounted on the base portion;
   e) a second portion of a pivot connection mounted on the proximal end of the digit and being connected to the first portion of the pivot connection;
   f) an actuator to cause pivotal movement of said digit around said pivot connection; wherein
   g) said base portion includes a second longitudinal axis X2 extending between said proximal side and said distal side of the base portion and a bearing between the base portion and said anchor portion and in which said base portion is mounted to said anchor portion via said bearing and rotatable with the digit about said second longitudinal axis X2; and
   h) including a rotation actuator for causing rotational movement of the digit within said bearing about said second longitudinal axis X2, wherein said rotational actuator comprises a motor mounted within the digit and including a torque tube connected at a first end to the rotational actuator and at a second end to the anchor.

2. A prosthetic device as claimed in claim 1, wherein said digit comprises a thumb.

3. A prosthetic device as claimed in claim 1 and having a palm portion and wherein said anchor portion is mounted on said palm portion.

4. A prosthetic device as claimed in claim 3 and including a plurality of prosthetic digits, said digits including:
   a. an anchor portion;
   b. a base portion having a proximal side and a distal side and being connected to said anchor portion;
   c. an elongate digit having a proximal end and a distal end and extending along a longitudinal axis X;
   d. a first portion of a pivot connection mounted on the base portion;
   e. a second portion of a pivot connection mounted on the proximal end of the digit and being connected to the first portion of the pivot connection; and
   f. a linear actuator within the elongate digit and having a first portion secured to the elongate digit for movement therewith and a second portion remote therefrom and axially movable relative thereto and being operable with said pivot connection, thereby to cause pivotal movement of said digit around said pivot connection upon axial movement of said second portion of said linear actuator.

5. A prosthetic device as claimed in claim 1 and including a plurality of prosthetic digits said digits including a rotation actuator for causing rotational movement of the digit within said bearing about said second longitudinal axis X2.

6. A prosthetic device as claimed in claim 1 and including a controller for controlling the operation of one or more of said digits.

7. A prosthetic device as claimed in claim 1 and including a first load sensor for sensing external resistance to pivotal movement of said one or more digits.

8. A prosthetic device as claimed in claim 1 and including a second load sensor for sensing external resistance to rotational movement of said one or more digits.

9. A prosthetic device according to claim 1 and wherein said prosthetic comprises a prosthetic thumb and a plurality of prosthetic fingers and wherein a controller operates to cause rotation of the prosthetic thumb in combination with pivotal movement of said thumb as said thumb moves towards said prosthetic fingers.

10. A prosthetic device as claimed in claim 1 and wherein said bearing comprises a hollow bearing having an internal aperture for receiving power or actuation connections.

11. A prosthetic device as claimed in claim 1 and including a linear actuator within the elongate digit and having a first portion secured to the elongate digit for movement therewith and a second portion remote therefrom, axially movable relative thereto and acting against the base portion being operable with said pivot connection, thereby to cause pivotal movement of said digit around said pivot connection upon axial movement of said second portion of said linear actuator.

12. A prosthetic device as claimed in claim 11, wherein said second portion of said linear actuator includes one or more transfer pivot pins extending outward therefrom and said base portion includes one or more apertures for receiving said one or more transfer pivot pins and wherein said apertures are radially displaced relative to the pivot connection such as to allow for pivotal movement of said digit about said pivot connection upon axial translation of said second portion of the linear actuator.

13. A prosthetic device as claimed in claim 11, wherein said base portion includes first and second sides projecting therefrom in a common direction D and being spaced apart from each other by an amount S and wherein each side includes a first portion of the pivot connection and wherein said digit includes a first side and a second side and wherein said first side includes a second portion of the pivot connection and said second side of the digit includes a second portion of the pivot connection and wherein each of said second portions of the pivot connection extend into respective first portions of the pivot connection.

14. A prosthetic device as claimed in claim 13, wherein said first side and second side of said digit are contained between said first and second sides of said base portion and wherein each of said first and second sides include, each of said slots extending along said longitudinal axis X of said digit and receiving respective second transfer pins therethrough.

15. A prosthetic device as claimed in claim 1 in which the torque tube extends through said bearing.

* * * * *